(12) United States Patent  (10) Patent No.: US 8,529,967 B2
Chaudhuri  (45) Date of Patent: *Sep. 10, 2013

(54) SUNSCREEN COMPOSITIONS AND METHODS

(75) Inventor: Ratan K. Chaudhuri, Lincoln Park, NJ (US)

(73) Assignee: Sytheon Ltd., Boonton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/280,550

(22) Filed: Oct. 25, 2011

(65) Prior Publication Data

US 2012/0039827 A1  Feb. 16, 2012

Related U.S. Application Data

(63) Continuation-in-part of application No. 11/803,188, filed on May 14, 2007, now abandoned.

(51) Int. Cl.
 *A61K 8/00* (2006.01)
 *A61Q 17/04* (2006.01)
(52) U.S. Cl.
 USPC .......................................... 424/725; 424/59

(58) Field of Classification Search
 USPC ............................................ 424/59, 757, 725
 See application file for complete search history.

(56) References Cited

U.S. PATENT DOCUMENTS 5,384,115 A * 1/1995 Bissett et al. ................... 424/59
2006/0251749 A1 * 11/2006 Jia et al. ......................... 424/757

* cited by examiner

*Primary Examiner* — Gina C Justice
(74) *Attorney, Agent, or Firm* — Edward K. Welch; IP&L Solutions

(57) ABSTRACT

Sunscreen compositions are provided for protecting skin from sun-induced damage comprising (i) at least one UV-B and/or UV-A/UV-B sunblock active, (ii) at least one meroterpene and (iii) a dermatological acceptable carrier wherein the meroterpene is free or substantially free of psoralens and has a purity of at least 90% w/w. Preferably, the sunblock active will be a UV-A/UV-B sunblock active. These skin protective compositions may optionally include an effective amount of one or more skin protective ingredients such as antioxidants, vitamins, anti-inflammatory agents, self-tanning agents and mixtures thereof.

20 Claims, No Drawings

SUNSCREEN COMPOSITIONS AND METHODS

This application is a Continuation-in-Part of pending U.S. patent application Ser. No. 11/803,188 filed on May 14, 2007.

FIELD OF THE INVENTION

This invention relates to sunscreen compositions for protecting skin from sun-induced damage comprising (i) at least one UV-B and/or UV-A/UV-B sunblock active, (ii) at least one meroterpene and (iii) a dermatological acceptable carrier. Most preferably, the sunblock active will be a UV-A/UV-B sunblock active with broad spectrum coverage. Optionally, said sunscreen compositions further comprise at least one UV-A sunblock active. Suitable meroterpenes are free or substantially free of furocoumarins, especially psoralens, and have a purity of at least 90% w/w. Especially preferred meroterpenes bakuchiol, corylifolin and substituted derivatives thereof. These skin protective compositions may optionally include an effective amount of one or more skin protective ingredients such as antioxidants, vitamins, anti-inflammatory agents, self-tanning agents, and mixtures thereof.

BACKGROUND OF THE INVENTION

As the outermost barrier of the body, the skin is directly exposed to a pro-oxidative environment. The effects of ultraviolet (UV) radiation from sun exposure can induce or exacerbate oxidative attack leading to the generation of reactive oxygen species (ROS) and other free radicals. The most prominent short-term effect of such skin exposure is a reddening of the skin (erythema): the most common consequence and evidence of sunburn. The most severe long-term consequence of photo-damage is skin cancer. Less severe long term photo-aging changes result in wrinkling, scaling, dryness, and uneven pigmentation consisting of hyper- and hypo-pigmentation (S R Pinneli, "Cutaneous Photodamage, Oxidative Stress, and Topical Antioxidant Protection", *J Am Acad Dermatol*, 48: 1-19, 2003; J Wenk, P Brenneisen, C Meewes, M Wlaschek, T Peters, R Blaudschwun, W. Ma, L. Kuhr, L Schneider, and K. Scharftetter-Kochanek, UV-Induced Oxidative Stress and Photoaging, in J Thiele and P. Elsner, Ede. Oxidants and Antioxidants in Cutaneous Biology, *Current Prob. Dermatol*. Basel, Karger, 29: 2001, pp 83-94; M Berneburg, H Plettenberg, and J Krutmann, Photoaging of Human Skin, *Photodermatol Photoimmunol Photomed*, 16: 239-244, 2000).

Extended life-span, more spare time and excessive exposure to UV radiation from sunlight or tanning devices, especially in the western population, has resulted in an ever increasing demand to protect human skin against the detrimental effects of UV-exposure. Sunscreens—the current gold standard of photo-protection—are useful, but their protection is most often inadequate due to improper and/or non-optimal application. Furthermore, most sunscreens are not suitably effective against long wave UV-A light due to the poor selectivity of most sunblock actives for UV-A and because UV-A is especially efficient at generating reactive oxygen species (ROS) (M Wlaschek, K Briviba, G P Stricklin, H Sies, K Scharfetter-Kochanek, *J Invest Dermatol*, 104: 194-198, 1995; M Berneburg, S Grether-Beck, V Kurten, T Ruzicka, K Briviba, H Sies and J Krutmann, Singlet Oxygen Mediates the UV-induced Generation of the Photoaging-Associated Mitochondrial Common Deletion, *J Biol Chem*, 274: 15345-15349, 1999; R Haywood, P Wardman, R Sanders and C Linge, Sunscreens Inadequately Protect Against Ultraviolet-A-Induced Free Radicals in Skin: Implications for Skin Aging and Melanoma, *J Invest Dermatol*, 121: 862-868, 2003). Although the principal focus of sunscreen products has traditionally been on UV-B due to its highly damaging nature, UV-A is being recognized increasingly as an important cause of photo-aging and skin cancer.

Furthermore, because, photo-aging of skin is a complex biological process affecting various layers of the skin with major changes seen in the connective tissue of the dermis, the natural shift toward a more pro-oxidant state in intrinsically aged skin can be significantly enhanced following UV-irradiation. Through the evaluation of punch biopsies of human skin following UV irradiation, Brennan et. al. have identified MMP-1 as the major collagenolytic enzyme responsible for collagen damage in photoaging (M Brennan, H Bhatti, K C Nerusu, N Bhagavathula, S Kang, G J Fisher, J Varani and J J Voorhees, Matrix Metalloproteinase-1 Is The Major Collagenolytic Enzyme Responsible for Collagen Damage in UV-Irradiated Human Skin, *Photochem Pholobiol*, 78: 43-48, 2003). In contrast, the synthesis of tissue inhibitory metalloprotease-1 (TIMP-1), the natural inhibitor of matrix metalloprotease, increases only marginally. This imbalance is one of the causes of severe connective tissue damage resulting in photo aging of the skin. Although collagen content decreases, collagen synthesis in sun-damaged skin appears to remain similar to that of sun-protected sites (A Oikarinen, M. Kallionen, Biochemical and Immunohistochemical Study of Collagen in Sun-Exposed and Protected Skin, *Photodermatology*, 6: 24-31, 1989; E Schwartz, F A Crickshank, C C Christensen, J S Perlish, and M Lebwohl, Collagen Alterations in Chronically Sun-Damaged Human Skin, *Photochem Photohiol*, 58: 841-844, 1993). Thus, evidence suggests that the decrease in collagen content in photo-damaged skin results from increased collagen degradation, by matrix metalloprotease, without significant changes in collagen production (E F Bernstein and J Uitto, The Effect of Photodamage on Dermal Extracellular Matrix, *Clinics in Dermatology*, 14: 143-151, 1996).

The damage caused by excessive MMP on the ECM proteins does not appear overnight, but results from the accumulation of successive instances of molecular damage, especially in the case of overexposure to UV light. The skin repercussion on the degradation of the ECM proteins may then be revealed in many ways depending on age, genetic predisposition, and life-style and, of course, on the general health status of the individual (A Oikarinen, The Aging of Skin: Chronoaging Versus Photoaging, Photderm, *Photoimmun. Photomed.*, 43: 3-4, 1990).

Whether extrinsic or intrinsic, these factors result in visible signs of skin aging and environmental damage, such as wrinkling and other forms of roughness (including increased pore size, flaking and skin lines), and other histological changes associated with skin aging or damage. The elimination of wrinkles has become a booming business in youth-conscious societies. Extrinsic or intrinsic factors may result in the thinning and general degradation of the skin. For example, as the skin naturally ages, there is a reduction in the cells and blood vessels that supply the skin. There is also a flattening of the dermal-epidermal junction which results in weaker mechanical resistance of this junction. See for example, Oikarinen, "The Aging of Skin: Chronoaging Versus Photoaging," *Photodermatol. Photoimmunol. Photomed.*, vol. 7, pp. 3-4, 1990, which is incorporated by reference herein in its entirety.

Many sunscreen preparations are sold commercially or are described in cosmetic or pharmaceutical literature. Ideally, sunscreen compositions should be nontoxic and non-irritating to the skin tissue and be capable of convenient application in a uniform continuous film. The product should be chemically and physically stable so as to provide an acceptable shelf life upon storage; and, it is particularly desirable that the preparation should retain its protective effect over a prolonged period after application. In general, sunscreen preparations are formulated as creams, lotions, oils or sprays containing, as the active agent, an inorganic additive that physically blocks the UV rays or an organic compound that absorbs ultra violet radiation, or combinations thereof. The sunscreen preparation works by blocking, physically or chemically, passage of ultra violet radiation thereby preventing its penetration into the skin.

According to Zecchino et al, (U.S. Pat. No. 5,008,100), sunblock active agents may be characterized in the order of decreasing effectiveness as either highly chromophoric (monomeric organic compounds and inorganic compounds such as titanium dioxide) and minimally chromophoric (polymeric organic solids).

Organic sunscreens are classified into UV-A filters, UVB filters or broad spectrum filters (UV-A and UVB functionality in a single molecule) depending on the type of radiation they absorb. UV-A sunscreens absorb radiation in the 320 to 400 nm regions of the ultra violet spectrum and UV-B sunscreens absorb radiation in the 290 to 320 nm regions of the ultra violet spectrum (See Sunscreens, Regulations and Commercial Development, Third Edition, Ed Nadim A. Shaath, Taylor & Francis, 2005), Broad-band sunscreens (UV-A and UVB functionality) absorb radiation in the 290 to 400 nm region of the ultra violet spectrum and have two maximums, one in the UV-B region and the other in the UV-A region, Representative references relating to UV sunscreens include Gonzalez et. al.—U.S. Pat. No. 7,186,404; Aust et. al.—U.S. Pat. No. 7,175,834; Roseaver et. al.—U.S. Pat. No. 7,172, 754; Simoulidis et. al.—U.S. Pat. No. 7,175,835; Mongiat et. al.—U.S. Pat. No. 7,101,536; Maniscalco—U.S. Pat. No. 7,078,022; Chaudhuri et. al.—U.S. Pat. No. 6,165,450; Forestier et. al. U.S. Pat. No. 5,175,340; and Wang et. al. U.S. Pat. No. 5,830,441.

Unfortunately, some of the highly chromophoric monomeric organic compounds employed in sunscreen compositions are not photostable and the protection from sun damage is lost after only a short period of time. For example, Avobenzone, a UV-A sunscreen, is generally photo-unstable. Furthermore, photo-instability of Avobenzone increases significantly when combined with Octyl methoxycinnamate (a UV-B organic sunscreen). In most studies, Octyl methoxycinnamte (OMC) has been regarded as relatively photostable. The absorption maxima of Avobenzone (about 360 nm) and OMC (about 310 nm) do not overlap sufficiently to allow directly excited singlet-singlet energy transfer to occur. However, transfer from one excited triplet-state to another is possible provided the energy levels are suitable. Techniques for stabilizing UV absorbent compositions are known. Representative disclosures in this area include Forestier et. al.—U.S. Pat. No. 5,567,418, U.S. Pat. No. 5,538,716, and U.S. Pat. No. 5,951,968; Deflandre et. al.—U.S. Pat. No. 5,670,140; Chaudhuri—U.S. Pat. No. 7,150,876, U.S. Pat. No. 6,831, 191, U.S. Pat. No. 6,602,515, U.S. Pat. No. 7,166,273, U.S. Pat. No. 6,936,735, U.S. Pat. No. 6,831,191, and U.S. Pat. No. 6,699,463; Chaudhuri et al.—U.S. Pat. No. 7,150,876; and Bonda et. al. U.S. Pat. No. 6,962,692.

In an effort to address some of the shortcomings of typical sunscreen compositions, certain manufacturers have added antioxidants. Antioxidants are believed to provide protection from free-radical damage by quenching or sequestering free radicals generated by UV exposure. Photo-protective products combining sunscreens and an antioxidant or antioxidant mixtures have been touted as providing increased efficacy and safety relative to UV exposure (S R Pitmen, Cutaneous Photodamage, Oxidative Stress, and Topical Antioxidant Protection, *J Am Acad Dermatol*, 48: 1-19, 2003). To be an effective quencher, it is believed that the antioxidant must be present in an adequate concentration at the site of free radical generation. However, since antioxidants are used in relatively low concentrations and are a separate ingredient, they may not be available at the site of free radical generation. Consequently, the level of skin protection may be reduced and, oftentimes, less than desired.

While the general use of antioxidants in sunscreen formulations is advocated, it is often disregarded that these compounds not only function as antioxidants, but intrinsically have pro-oxidant action as well, especially in the presence of transition metals (See e.g., "Role of Antioxidants in Sun Care Products" by R. Chaudhuri in Sunscreens, N A Shaath, editor, Taylor and Francis, p 603-638, 2005). There is pro-oxidant action even in well-known antioxidants, such as, vitamin C (ascorbate), vitamin E (tocopherols), glutathione and proanthocyanidins (from pine and grape). The pro-oxidant activity of vitamin C results from the reduction of $Fe^{3+}$ to $Fe^{2+}$ and its reaction with $H_2O_2$ to generate OH radicals. Pro-oxidant effects are not unique to vitamin C: they can be demonstrated with many reducing agents, including vitamin E, glutathione and several plant phenolic compounds, in the presence of transition metal ions. Thus, if vitamin C's pro-oxidant effects are relevant, the pro-oxidation effects of these other reductants may also be expected to occur.

While the objective of sunscreens is, in general, to prevent skin damage due to UV exposure, such also prevents, in many instances, the skin darkening effect, or tanning, desired by many sunbathers. So as not to completely disappoint those desirous of a bronze look, formulators oftentimes add self-tanning agents such as dihydroxyacetone (DHA) to their sunscreen compositions. DHA is an intermediate of carbohydrate metabolism in higher plants and animals: commonly present as the dihydroxyacetone monophosphate in glycolysis. In crystalline form, DHA is a mixture of one monomer and four dimers: though an all monomer form may be generated by heating or melting dimer DHA or by dissolving it in water.

The reaction product of DHA and the skin protein that produces the "tan" color has been shown to provide protection against UV-A in animals and humans (Self-Tanners: Formulating with Dihydroxyacetone, R. Chaudhuri & C Hwang, *Cosmetics & Toiletries*, 116:87-96, 2001; Dihydroxyacetone: Chemistry and Applications in Self-Tanning Products, R. Chaudhuri, in The Chemistry and Manufacture of Cosmetics, Ed, M Schlossman, Allured publishing, 3rd Edition, 383-402, 2002). Experimental and clinical evidence show that skin that has been treated topically with 3% DHA solution overnight has a Sun Protection Factor (SPF) of at least 3 in the UV-B region. Likewise, a photoprotection factor of 10 in the UV-A region has been observed with 15% solution of DHA. Unfortunately, DHA is photochemically very unstable and it takes a long time to get a very little skin protection against sun-induced skin damage (Self-Tanners: Formulating with Dihydroxyacetone, R. Chaudhuri & C Hwang, *Cosmetics & Toiletries*, 116:87-96, 2001).

Despite all the efforts that have been undertaken to formulate effective sunscreen compositions and despite the constant reminders of the importance of proper and adequate application, current sunscreen products are not entirely effective. Either the formulation is not fully effective, or at least not at the time of application, or its application is faulty or improper: most often a little of both. Presently available sunscreen compositions are, for the most part, ineffective against Reactive Oxygen Species induced and/or enzyme induced skin damage. Additionally, the products are oftentimes chemically and physically unstable, having poor or moderate shelf life upon storage and/or fail to retain its protective effect over a prolonged period after application. Furthermore, it is merely a matter of reality that those who apply the sunscreen often do so improperly or ineffectively: particularly when it comes to the timely re-application of the sunscreen product and/or its re-application following certain activities, such as swimming, washing face and hands, etc. Consequently, the user oftentimes finds him or herself with a sunburn, and the concomitant underlying damage manifested by the sunburn inducing UV exposure, despite their best efforts.

Thus, there is a continuing need and effort to formulate sunscreen compositions that are more effective and more forgiving and have improved physical and chemical stability.

Furthermore, since sunscreens are not utopian and there is and always will be the human factor relative to their application, it would also be especially desirable to provide a sunscreen product that not only protects one's skin from the damaging effects of UV exposure, but also improves the health and/or physical appearance of the skin and/or repairs past skin damage, whether due to UV exposure or merely as a result of natural aging.

Surprisingly, it has now been found that effective sunscreen compositions having many, if not most, of the desired attributes of the utopian, or nearly utopian, sunscreen composition may be prepared by the further incorporation therein of an effective amount of one or more purified meroterpenes or meroterpene enriched extracts.

Furthermore, it has now been found that the combination of traditional sunblock actives and meroterpenes or enriched meroterpene extracts in a sunscreen composition provide a performance synergy in preventing damage due to UV exposure as well as in mitigating the manifestation of said damage, particularly in the short term time frame. These compositions also have improved stability and utility in many cosmetic applications, enabling sunscreen application concurrent with one's application of their cosmetics

SUMMARY

According to the present invention there are provided novel sunscreen compositions for protecting skin from sun-induced damage comprising (i) at least one UV-B and/or UV-A/UV-B sunblock active, (ii) at least one meroterpene, and (iii) a dermatologically acceptable carrier wherein the meroterpene is free or substantially free of furocoumarins, especially psoralens and has a purity of at least 90% w/w. Preferably, the sunblock active will be a UV-A/UV-B sunblock active with a broad-spectrum coverage. Suitable meroterpenes include purified meroterpenes. Especially preferred sunscreen compositions are those based on the meroterpene bakuchiol, corylifolin or derivatives thereof which are free or substantially free of psoralens, especially psoralene and isopsoralene.

The sunscreen compositions of the present invention will typically comprise the sunblock actives in their conventional amounts and the meroterpene in an amount of from about 0.1 to about 10 wt %, preferably from about 0.5 to about 5 wt % based on the total weight of the sunscreen composition. Additionally, these sunscreen compositions may optionally include an effective amount of one or more skin protective and/or treatment ingredients such as antioxidants, vitamins, anti-inflammatory agents, self-tanning agents, moisturizers, emollients, humectants, and the like, and mixtures thereof, in their conventional amounts. The sunscreen compositions of the present invention are applied topically and may take the form of a lotion, spray, ointment, gel, or other topically applicable form.

The present invention is also directed to a method of preventing skin damage arising from exposure to UV radiation, said method comprising the step of applying a sunscreen composition comprising (i) at least one UV-B and/or UV-A/UV-B sunblock active, (ii) at least one meroterpene, and (iii) a dermatologically acceptable carrier, wherein the meroterpene is free or substantially free of furocoumarins, especially psoralens, and has a purity of at least 90% w/w, to the exposed skin Preferably, the method comprises the step of applying the sunscreen composition to the skin prior to exposing it to sunlight, most preferably at least 15 minutes prior to the exposure. Furthermore, the method may also, and preferably does, include the step of re-applying the sunscreen composition periodically, preferably at least every couple of hours, and/or following participation in those activities that may wash or wear away the sunscreen composition already applied to the skin.

The present invention also relates to a method of preventing skin damage due to UV exposure concurrent with the treatment of skin damage due to various disease conditions and/or aging and/or long-term exposure to UV light said method comprising the step of applying a sunscreen composition comprising (i) at least one UV-B and/or UV-A/UV-B sunblock active, (ii) at least one meroterpene, and (iii) a dermatologically acceptable carrier, wherein the meroterpene is free or substantially free of furocoumarins, especially psoralens, and has a purity of at least 90% w/w, to those areas of the skin showing evidence of the disease condition and/or prior damage from UV exposure.

In each of the foregoing embodiments, the sunscreen compositions and the sunscreen compositions employed in the recited methods further comprise a UV-A sunblock active as an optional component.

The sunscreen compositions according to the present provide improved performance as compared to sunscreen compositions without the meroterpenes, especially meroterpene sunscreen compositions which are not free or substantially free of furocoumarins, especially psoralens and fail to have a purity of at least 90% w/w. In particular, these compositions do not show an enhanced adverse response to UV exposure, as might be expected with meroterpenes generally, especially those that are not free or substantially free of furocoumarins, and provide benefits not attained by sunscreen compositions in the absence of the meroterpenes. Furthermore, the present sunscreen compositions have excellent and improved stability, utility and acceptability as compared to similar compositions having a meroterpene whose purity is less than required by the present teachings. These and other features, aspects, and advantages of the present invention will become evident to those skilled in the art from reading of the present disclosure.

DESCRIPTION OF THE INVENTION

As used herein and in the appended claims, the phrase "substantially free of" means that the recited compound or component, if present, is present at an inconsequential generally less than 0.1 wt % based on the weight of the meroterpene, and does not interfere with the performance of the sunblock additive or the meroterpene. Most preferably, the amount, if present will be insufficient to manifest any visible skin damage, including erythema, following exposure to UV light at levels which would manifest such damage with the same formulation containing the recited compound at its conventional concentration. The term "dermatologically-acceptable", as used herein, means that the compositions or components thereof so described, as well as the compositions containing said components, are suitable for use in contact with human skin without undue toxicity, incompatibility, instability, allergic response, and the like. Further, it is to be appreciated that the terms "furocoumarin" and "furanocoumarin" are used interchangeably in the specification and claims: the latter being the more technically correct term. Finally, all publications and patents references, including published patent applications, referenced herein are hereby incorporated herein in their entirety.

The first of the two critical ingredients of the sunscreen compositions of the present invention is the presence of a sunblock active that either absorbs or physically blocks UV-B radiation, e.g., UV-B and/or UV-A/UV-B sunblock actives. UV-B is the most damaging of ultraviolet radiation and, therefore, is the most important one to address. Also, because there are those who still desire a "natural" tan, the absence of a significant amount of UV-A sunblock active or a strongly UV-A type UV-A/UV-B sunblock active will still provide some protection against the harmful effects of UV exposure while still allowing the "tanning" waves to do their stuff. Indeed, such formulations may also contain an active ingredient that promotes tanning by amplifying the effects of UV light, e.g., melanin, L-tyrosine, tea oil, and green tea extracts. Most preferably, though, particularly since self-tanning agents such as DHA can be added to the sunscreen compositions, the sunscreen compositions of the present invention will be effective against both UV-A and UV-B and have either strong UV-A/UV-B sunblock actives or the presence of an additional UV-A sunblock active.

As noted earlier, sunblock actives are of two types, inorganic actives that work by reflecting the UV light and organic actives that work, predominately, by absorbing UV energy. The amount of the sunblock active to be incorporated into the sunscreen formulations is that which is conventional in the art. Typically, the amount is dependent upon, among other factors, the delivery means, e.g., is it applied as a spray or lotion; the stability of the active; the efficacy of the selected sunblock active itself; and the application rate, as well as the particular SPF desired. From the commercial perspective, another factor influencing the level of such sunblock actives in the sunscreen formulations is the regulatory limitations on their use. In the United States, for example, strict controls are placed upon the maximum level at which approved sunblock actives may be present. Similar regulatory/governmental controls may also dictate which sunblock actives may be used and at what amount in other countries as well.

Suitable organic sunblock actives include, for example, avobenzone, butyl methoxydibenzoylmethane, cinoxate, benzophenone-8, dioxybenzone, homosalate, octylsalate, menthyl anthranilate, octocrylene, ethyhexyl methoxycinnamate, octyl methoxycinnamate, octyl salicylate, oxybenzone, padimate O, ethylhexyl salicylate, benzophenone-3, p-aminobenzoic acid (PABA), ethythexyl dimethyl PABA, glyceryl PABA, phenylbenzimidazole sulfonic acid, sulfisobezone, trolamine salicylate, 4-methylbenzylidene camphor, bisoctrizole, bemotrizinol, ecamsule, drometrizole trisitoxane, disodium phenyl dibenzimidazole tetrasulfonate, diethylamine hydroxybenzoyl hexyl bezoate, triazone, hexyl benzoate, benzophenone-4, ethyhexyl triazone, diethylhexyl butamido triazone, bisimidazylate, polysilicone-15, etc.

Inorganic sunscreens include, but are not limited to, microfine surface treated titanium dioxide and microfine untreated and surface treated zinc oxide. The titanium dioxide in the sunscreen compositions preferably has a mean primary particle size of between 5 and 150 nm, preferably between 10 and 100 nm. Titanium oxide may have an anatase, rutile, or amorphous structure. The zinc oxide in the sunscreen compositions preferably has a mean primary particle size of between 5 nm and 150 nm, preferably between 10 nm and 100 nm. Examples of suitable hydrophobically modified titanium dioxide compositions include but are not limited to the following:

UV Titans® X161, M160, M262 (surface treated with stearic acid and alumina) (Kendra)

Eusolex® T-2000 (surface treated with alumina and simethicone) (Merck KGaA)

T-Cote® (surface treated with dimethicone) (BASF)

Mirasun® TiW60 (surface treated with silica and alumina) (Rhodia)

Tayaca MT100T (surface treated with aluminum stearate) (Tayaca)

Tayaca MT-100SA (surface treated with silica and alumina) (Tayaca)

Tayaca MT-500SA (surface treated with silica and alumina) (Tayaca)

Tioveil® EUT, FIN, FLO, FPT, GCM, GPT, IPM, MOTG, OP, TG, TGOP (surface treated with silica and alumina, 40% dispersion in a range of cosmetic vehicle) (ICI)

Eusolex® T-45D (surface treated with alumina and simethicone, 45% dispersion in isononoylnonaoate) (Merck KGaA)

Eusolex® T-Aqua (surface treated with aluminum hydroxide, 25% dispersion in water) (Merck KGaA)

Examples of suitable untreated and hydrophobically modified zinc oxide include but are not limited to the following:

Z-Cote® (uncoated microfine zinc oxide) (BASF)

Z-Cote® HP-1 (surface treated with dimethicone) (BASF)

Sachtotec® LA 10 (surface treated with lauric acid) (Sachtleben)

Sachtotec® (uncoated microfine zinc oxide) (Sachtleben)

Spectraveil® FIN, IPM, MOTG, OP, TG, TGOP (uncoated, 60% dispersion in a range of cosmetic vehicle) (ICI)

Z-sperse® TN (untreated, dispersion in C12-15 alkyl benzoate) (Collaborative)

Z-sperse® TN (untreated, dispersion in octydodecyl neopentanoate) (Collaborative)

Most preferably, the sunscreen compositions of the present invention will comprise a combination of such sunblock actives. In this respect, it is well known that certain sunblock actives have better stability, hence longevity, than others; while others have better absorptive capabilities, whether in reference to selectivity for certain UV energy of certain wavelength(s) or cumulative absorptive capabilities. Hence, by using combinations of such UV sunblock actives, one is able to provide greater protection. Suitable combinations are well known in the art and within the skill of a typical artisan in the field.

The second critical component of the sunscreen compositions of the present invention is the meroterpene. Meroterpenes are terpenes having an aromatic ring and are generally of the following chemical structure (I):

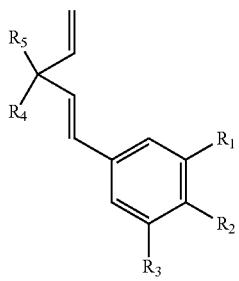

wherein $R_1$, $R_2$, and $R_3$ are each independently selected from the group consisting of H, OH, $OR_6$ or $CH_2R_6$ where $R_6$ is linear or branched $C_1$ to $C_8$ alkyl; and $R_4$ and $R_5$ are each independently a linear or branched, $C_1$ to $C_{20}$ alkyl or alkenyl group. Exemplary meroterpenes include Bakuchiol wherein $R_1$=$R_3$=H; $R_2$=OH, $R_4$=$CH_3$; $R_5$=$CH_2CH_2CH$=C$(CH_3)_2$ and Corylifolin wherein $R_1$=$R_1$=H; $R_2$=OH, $R_4$=$R_5$=$CH_3$.

Meroterpenes are typically derived from plants and plant extracts, though they have also been obtained from fungi as well as produced synthetically. Plants and plant extracts, though, remain the most common source of these compounds with *Psoralea coryfolia, Psoralea grandulosa*, and *Otholobium pubescens* (Fabaceae) being the more common of such plant sources. In the practice of the present invention, the meroterpene may be added as an isolated or purified material of at least 90% purity w/w, most preferably at least 95% pure w/w. High purity, at least 90% is especially important for commercially viable products owing to the color and instability issues associated with the less purified materials. Specifically, the less pure materials, even those of about 85% purity, are not commercially acceptable as a component of sunscreen compositions or cosmetic compositions that also incorporate sunscreen actives owing to the coloration and, consequently, difficulty in formulating acceptable or acceptable colored products for the typical consumer. Regardless of the nature or form of the meroterpene, the meroterpene must be free or substantially free of furocoumarins, especially psoralens such as psoralene and isopsoralene, and other like compounds that are skin sensitizers and/or enhance the detrimental effect of UV exposure. Because the furocoumarins are found in the same plants and extracts from which meroterpenes are recovered, they are typically present in commercial grade meroterpenes and meroterpene extracts. For example, psoralens, including isopsoralens, typically comprise 0.1 to 2% of the dry weight of the plant and seed source materials and from 1.0 to 20% by weight of the crude extracts thereof in organic solvents such as ethanol.

The preferred meroterpene for use in the practice of the present invention is bakuchiol, Bakuchiol is a known bioactive material and has been used as an anti-tumor agent, an antimicrobial agent, an anti-inflammatory agent, a skin whitening agent, etc. It, in combination with pyridine aldehyde, has also been used in the treatment of pimples, acne, blackheads, herpes, and other skin disorders, However, its use is limited or at least tempered by the presence of high levels of psoralene and other furocoumarins. Although psoralene is also a strong bio-active agent,—it is used in combination with UVA for the treatment of psoriasis and eczema—it greatly enhances the sensitivity of skin to the effects of UV exposure, significantly increasing the potential for sunburn. Consequently, the use of bakuchiol and other meroterpenes, particularly those derived from plant sources, as a treatment has been limited to circumstances where sun exposure is not of concern or where precautions are taken to avoid sun exposure following treatment.

Recent developments, however, have been made in meroterpene production and recovery enabling one to prepare meroterpenes that are free or substantially free of furocoumarins, especially psoralens like psoralene and isopsoralene. For example, Indian patent publication #00570/KOL/2005, (filed Jun. 29, 2005 and published on Jan. 13, 2006) which is incorporated herein by reference in its entirety, describes a method of purifying Bakuchiol from the extract of *Psoralea corylifolia* seeds. The method involves extraction of the plant material (powdered seeds) with a non-polar solvent like hexane or heptane. The extract solution is then treated with an alkali solution such as an alkali metal carbonate, bicarbonate or hydroxide to provide 3-layered volume liquid, an organic layer, an emulsion layer and an aqueous layer. The organic layer is washed with water and dilute HCl and concentrated to a viscous mass. Concurrently, the emulsion layer is dissolved in a polar solvent like ethyl acetate and separated to remove the so-formed aqueous layer. The aforementioned viscous mass is then mixed with the ethyl acetate solution and concentrated to remove ethyl acetate and traces of the non-polar solvent. The concentrated mass is then subjected to high vacuum distillation, generally 1 mm to 0.1 mm at 139° C. to 175° C. That fraction collected between the oil bath temperature of 190-270° C. and vapor temperature range of 140-180° C. is found to contain pure Bakuchiol, free or substantially free of psoralene and isopsoralene as well as other known constituents of such plant extracts such bavachicin, bavachin, angelicin, isobavachalcone, bakuchcin, and the like.

An alternate method for the preparation of bakuchiol that is free or substantially free of impurities, particularly furocoumarin impurities, is described in Jia et. al.—US 2006/0251749, which is incorporated herein by reference in its entirety. Jia et al. describes a method wherein the plant source materials are subjected to an extraction and the extract solutions are then subject to hydrolysis with a basic solution such as aqueous sodium hydroxide. The resultant product is then purified by one of column chromatography, extraction followed by crystallization, solvent partition, recrystallization, and combinations of the foregoing. Crude extracts purified in this way are said to be essentially free of furocoumarins such as psoralene and isopsoralene. These purified products are said to have purities of from 14 to 100%, more typically from 27% to 100%. Unlike the present applicant, Jia et. al. fail to attribute or recognize any importance, significance or criticality to the overall purity of its products: thus, the satisfaction with such broad ranges on purity. This is most evident form the Jia et. al. prosecution during which Jia et. al. specifically argued and taught that high purity, especially higher than 90%, is not necessary for performance or efficacy and efforts to attain high purity is unwarranted. Applicant, however, has found such purity to be especially important and critical for the preparation of sunscreen compositions, including sunscreen effective cosmetic compositions. Thus, the Jia et. al. teachings are applicable to the present invention insofar as they relate to the production of the psoralen free, high purity products.

Other publications or patents that describe isolation or synthesis of meroterpenes include:

C N Backhouse, C L Delporte, R E Negrete, S Erazo, A Zuniga, A Pinto, B K Cassels, *J Ethnopharmacology*, 78(1):27-31, 2001, Haraguchi, J Inouye, Y Tamara, K Mizutani, *Planta Medica*, 66(6):569-571, 2000, J M Krenisky, J Luo, M J Reed, J R Carney, *Biol. Pharm Bull,* 22(10):1137-1140, 1999.

H Katsura, R Tsukiyama, A Suzuki, M Kobayashi, *Antimicrobial Agents and Chemotherapy,* 45(11):3009-3013, 2001.

S Adhikari, R Joshi, B S Patro, T K Ghanty, G J Chintalwar, A Sharma, S Chattopadhaya, T Mukherjee, *Chem Res Toxicol,* 16:1062-1069, 2003, J B Perales, N F Makino, D L Van Vranken, *J Org Chem,* 67:6711-6717, 2002, all of which are incorporated herein by reference in their entirety. These purified meroterpenes, especially the purified bakuchiol, may be obtained from Sytheon Ltd., of Boonton, N.J., USA, The meroterpene is present in the sunscreen compositions in an effective amount, that is, in an amount that reduces erythema from UV exposure as compared to the same formulation without the meroterpene. Generally speaking, sunscreen compositions according to the present invention will contain from about 0.1 to about 10, preferably from about 0.5 to about 5, weight percent of the meroterpene based on the total weight of the sunscreen composition. With this level of use, the visual manifestation of erythema following short term exposures to UV light may be avoided altogether as compared to sunscreen formulations without the meroterpene; whereas, longer exposures will result in erythema, but less pronounced and/or shorter lived as compared to sunscreen formulations without the meroterpene. When the meroterpene is added as a purified plant extract or as a purified material that also contains other components, the weight percent is based on the meroterpene content itself.

The third and final key component of the sunscreen compositions of the present invention is the carrier. The carrier is that material or combination of materials that is used to essentially carry or deliver the sunblock active(s) and meroterpenes to the skin. The specific carrier material will depend upon the delivery method itself. For example, as mentioned earlier, the sunscreen compositions may be in the form of lotions, creams, gels, foams, emulsions, dispersions, sprays, liposomes, coacervates, etc. Each composition will typically include any of the known topical excipients and like agents necessary for achieving the particular form, such excipients include, e.g., mineral oils and emulsifying agents. In its most simplest of embodiments, the carrier may be water, alcohol or water/alcohol combinations, or other solvent(s) or solvent systems in which the aforementioned actives may be, e.g., soluble, dispersed, emulsified, etc. Preferably, though, the sunscreen compositions will include excipients and the like that create a substantially stable, homogenous sunscreen compositions and/or provide body and viscosity to the sunscreen composition so that the actives do not merely run off the skin once applied. Typically, the carrier will comprise from about 30 to about 99% by weight of the sunscreen composition.

Generally speaking, any known carrier or base composition employed in traditional sunscreen compositions may be used in the practice of the present invention. Suitable carriers and carrier compositions are described at length in, for example, Gonzalez et. al.—U.S. Pat. No. 7,186,404; Aust et. al.—U.S. Pat. No. 7,175,834; Roseaver et. al.—U.S. Pat. No. 7,172,754; Simoulidis et. al.—U.S. Pat. No. 7,175,835; Mongiat et. al.—U.S. Pat. No. 7,101,536; Maniscalco—U.S. Pat. No. 7,078,022; Forestier et. al.—U.S. Pat. No. 5,175,340, U.S. Pat. No. 5,567,418, U.S. Pat. No. 5,538,716, and U.S. Pat. No. 5,951,968; Deflandre et. al.—U.S. Pat. No. 5,670,140; Chaudhuri—U.S. Pat. No. 6,831,191, U.S. Pat. No. 6,602,515, U.S. Pat. No. 7,166,273, U.S. Pat. No. 6,936,735, and U.S. Pat. No. 6,699,463; Chaudhuri et. al.—U.S. Pat. No. 6,165,450 and U.S. Pat. No. 7,150,876; Bonda et, at U.S. Pat. No. 6,962,692; and Wang et. al. U.S. Pat. No. 5,830,441, all of which are incorporated herein by reference in their entirety. Those skilled in the art will readily recognize and appreciate what carriers may be employed in light of the intended form and/or delivery method for the inventive sunscreen compositions.

Though a carrier by itself is sufficient, the inventive sunscreen compositions of the present invention may, and preferably will, contain various other components typically associated with skin care products. For example, various skin care agents including, but not limited to, conventional skin care excipients as well as additional photoprotective agents and skin lightening agents may be present. Such agents include, but are not limited to antioxidants, vitamins, anti-inflammatory agents, self-tanning agents, moisturizers, emollients, humectants, and the like, and mixtures thereof, in their conventional amounts. Exemplary agents and additive materials are described briefly below as well as in the aforementioned patents, especially Maniscalco—U.S. Pat. No. 7,078,022.

Suitable antioxidants include, but are not limited to, water-soluble antioxidants such as sulfhydryl compounds and their derivatives (e.g., sodium metabisulfite and N-acetyl-cysteine), lipoic acid and dihydrolipoic acid, resveratrol, lactoferrin, and ascorbic acid and ascorbic acid derivatives (e.g., ascorbyl palmitate and ascorhyl polypeptide). Oil-soluble antioxidants suitable for use in the compositions of this invention include, but are not limited to, butylated hydroxytoluene, retinoids (e.g., retinol and retinyl palmitate), tocopherols (e.g., tocopherol acetate), tocotrienols, alkylresorcirtols, curcurmin and its derivatives and ubiquinone. Natural extracts containing antioxidants suitable for use in the compositions of this invention, include, but not limited to, extracts containing flavonoids and isoflavonoids and their derivatives (e.g., genistein and diadzein), extracts containing resveratrol and the like. Examples of such natural extracts include grape seed, green tea, pine bark, *Phyllanthus emblica* and propolis. Other examples of antioxidants may be found on pages 1612-13 of the ICI Handbook as well as in Ghosal—U.S. Pat. No. 6,124, 268, both of which are incorporated herein by reference in their entirety.

The sunscreen compositions of the present invention may also include one or more vitamins and/or their derivatives. Vitamins and vitamin derivatives include, for example, vitamin A, vitamin A propionate, vitamin A palmitate, vitamin A acetate, retinol, vitamin B, thiamine chloride hydrochloride (vitamin B.sub.1), riboflavin (vitamin B.sub.2), nicotinamide, vitamin C and derivatives (for example ascorbyl palmitate, magnesium ascorbyl phosphate, ascorbyl acetate), vitamin D, ergocalciferol (vitamin D.sub.2), vitamin E, DL-.alpha.-tocopherol, tocopherol E acetate, tocopherol hydrogensuccinate, vitamin K.sub.1, esculin (vitamin P active ingredient), thiamine (vitamin $B_1$), nicotinic acid (niacin), pyridoxine, pyridoxal, pyridoxamine, (vitamin $B_6$), pantothenic acid, biotin, folic acid and cobalamine (vitamin $B_{12}$). Preferred vitamins are, for example, vitamin A palmitate, vitamin C and derivatives thereof, DL-α-tocopherol, tocopherol E acetate, nicotinic acid, pantothenic acid and biotin. Vitamin E, which is often added to cosmetic and personal care products is also preferably stabilized by the compounds according to the invention. Additional preferred vitamins are Vitamin C and K and derivatives thereof.

Suitable emollients include those agents known for softening the skin which may be selected from hydrocarbons, fatty acids, fatty alcohols and esters. Petrolatum is a common hydrocarbon type of emollient conditioning agent. Other hydrocarbons that may be employed include alkyl benzoate, mineral oil, polyolefins such as polydecene, and paraffins, such as isohexadecane. Fatty acids and alcohols typically have from about 10 to 30 carbon atoms. Illustrative are myristic, isostearic, hydroxystearic, oleic, linoleic, ricinoleic, behenic and eruicic acids and alcohols. Oily ester emollients may be those selected from one or more of the following, triglyceride esters, acetoglyceride esters, ethoxylated glycerides, alkyl esters of fatty acids, ether esters, polyhydric alcohol esters and wax esters. Additional emollients or hydrophobic agents include $C_{12}$ to $C_{15}$ alkyl benzoate, dioctyladipate, octyl stearate, octyldodecanol, hexyl laurate, octyldodecyl neopentanoate, cyclomethicone, dicapryl ether, dimethicone, phenyl trimethicone, isopropyl myristate, capriylic/capric triglycerides, propylene glycol dicaprylate/dicaprate and decyl oleate.

Suitable humectants include various polyhydric alcohols, especially polyalkylene glycols and, more preferably, alkylene polyols and their derivatives. Exemplary humectants include propylene glycol, dipropylene glycol, polypropylene glycol, polyethylene glycol, sorbitol, 2-pyrrolidone-5-carboxylate, hydroxypropyl sorbitol, hexylene glycol, ethoxydiglycol 1,3-butylene glycol, 1,2,6-hexanetriol, glycerin, ethoxylated glycerin, propoxylated glycerin, compatible solutes, such as ectoin, hydroxectoin, taurines, carnithine, acetyl carnithine and mixtures thereof. When employed in effective amounts, generally from 1 to 30%, preferably from 2 to 20%, by weight of the sunscreen composition, these additives serve as skin moisturizers as well as reduce scaling and stimulate the removal of built-up scale from the skin.

Examples of anti-inflammatory ingredients include, but are not limited to, bisabolol, curcurmin and its derivatives, retinoids, flavonoids and other polyphenolics etc. These and other anti-inflammatory agents, as well as additional antioxidants and the like, are disclosed in Gupta et. al.—US 2005/0048008A1, which is incorporated herein by reference in its entirety.

Examples of self-tanning ingredients include, but are not limited to, dihydroxyacetone and erythrulose.

The sunscreen compositions of the present invention may also include one or more skin penetrants. These are additives that, when applied to the skin, have a direct effect on the permeability of the skin barrier: increasing the speed with which and/or the amount by which certain other compounds are able to penetrate into the skin layers. Exemplary organic penetration enhancers include dimethyl sulfoxide; isopropyl myristate; decyl, undecyl or dodecyl alcohol; propylene glycol; polyethylene glycol; $C_{9-11}$, $C_{12-13}$ or $C_{12-15}$ fatty alcohols; ozone; alkyl pyrrolidones; dialkyl isosorbides, lecithin; etc. Surfactants can also be used as penetration enhancers. In the case of meroterpenes, penetrants have the benefit of carrying the meroterpene into the skin faster than it might otherwise penetrate on its own: thereby expediting and, possible, enhancing the benefit of the meroterpene.

Other optional adjunct ingredients for the sunscreen compositions of the present invention include preservatives, waterproofing agents, fragrances, anti-foam agents, plant extracts (Aloe vera, witch hazel, cucumber, etc), opacifiers, stabilizers, skin conditioning agents colorants, and the like, each in amounts effective to accomplish their respective functions.

The sunscreen compositions of the present invention are effective in reducing or preventing skin damage due to UV exposure, especially exposure to the sun. As such, the present invention also pertains to a method of protecting skin from damage due to UV exposure said method comprising the step of applying of the aforementioned sunscreen compositions to skin. In particular, the present invention provides a method of reducing or preventing erythema resulting from exposure to UV light. Generally speaking, the method comprises the step of applying the sunscreen composition to areas of the skin that are or may be exposed to the sun. It may also be desirable to apply the sunscreen composition to areas that are not typically exposed to the sun but that nevertheless have exposure to the penetrating UV rays. For example, tee shirts and other light fabrics offer minimal protection against sun exposure, especially to UV rays. Thus, conceivably, the inventive sunscreen compositions may be applied to essentially all areas of the body, including those typically covered by clothing.

The amount of the sunscreen composition that is to be applied to the skin is consistent with that amount applied with respect to sunscreen formulations without the meroterpene. To some extent, the amount depends upon the form of the sunscreen composition and its mode of application. For example, a spray formulation may be applied so as to provide a light, even coat on the skin. Lotions, creams, gels and the like are typically applied at a rate of about 1 to 2 ounces for the entire body, i.e., for the exposed skin of a "average individual" wearing a swimsuit and standing 5 feet 4 inches tall, weighing 150 pounds, and having a 32 inch waist. This translates to an application rate of about 2 mg/cm$^2$ of skin. On the face, a typical application rate is ¼ to ⅓ of a teaspoon. Generally speaking, the application rate will be from about 0.1 to about 10 mg/cm$^2$, preferably from about 1 to about 3 mg/cm$^2$, of skin.

To be most effective, the sunscreen composition should be applied before sun exposure, preferably at lest 15 minutes before, and reapplied at least every 2 hours or more frequently, especially if the individual engages in activities/ actions that may cause the sunscreen composition to wear or wipe off, e.g., swimming; washing dishes, windows, etc.; washing hands and/or face; contact sports activities; activities that promote substantial sweating; etc.

In addition to the above-mentioned photo-protective benefits of the inventive sunscreen compositions, the continual, preferably daily, use of the sunscreen compositions of the present invention, regardless of whether one anticipates UV exposure or not, provides a number of additional benefits to ones skin. For example, the continual use of these sunscreen compositions will delay the appearance of fine lines, enhance extracellular matrix cohesion, reduce the appearance of spider veins, improving skin firmness and elasticity: skin effects that are not only a result of exposure to the sun but also the natural aging process. In essence, the long-term benefits of the continual use of the sunscreen compositions of the present invention include the lessening or delayed manifestation, possibly even the prevention or repair, of skin damage and will manifest itself in an overall improved skin quality as compared to skin on which meroterpene-free sunscreens had been applied and, most especially, to which no sunscreen product had been applied on an on-going basis. For example, the long-term use of the inventive sunscreen compositions may help with thickening the keratinous tissue (i.e., building the epidermis and/or dermis layers of the skin), thereby preventing and/or retarding atrophy of human skin; preventing and/or retarding the appearance of spider veins and/or red blotchiness on human skin; preventing and/or retarding the appearance of dark circles under the eye; preventing and/or retarding sallowness and/or sagging of human skin; soften and/or smooth lips; preventing and/or relieving itch of human skin, regulating skin texture (e.g. wrinkles and fine lines), improving skin color (e.g. redness, freckles); and the like.

EXAMPLES

Having described the invention in general terms, Applicants now turn attention to the following examples in which specific formulations and applications thereof are evaluated. In the foregoing and in the following examples, unless otherwise indicated, all temperatures are set forth in degrees Celsius and all parts and percentages are by weight.

Bakuchiol and Corylifolin

Purified Bakuchiol and Corylifolin for use in the following examples were obtained by the method described by R K Tikare and P Pujari (Indian patent application 00570/KOL/2005; publication date Jan. 13, 2006), Specifically, seeds of *Psoralea Corylifolia* were powdered and subjected to extraction using a non-polar solvent, hexane, in a ratio of 3 ml solvent for each gram of powdered seed. The mix was stirred with heating at 60° C. for 4 hrs and then filtered to separate the extract solution. The extraction was repeated three more times, for a total of four extractions on each sample of the powdered seed material, to increase the yield. Extract solution collected from all four batches was combined and the total volume reduced by distilling off excess solvent until the remaining volume was about one-half the original volume. The concentrated solution was then treated/washed with 7.5 L of an alkali solution (5% NaOH) twice. The alkali treatment produced three layers: an organic layer, an emulsion layer and an aqueous layer. The organic layer was washed with an equal volume of water and dilute HCl and subsequently concentrated to produce a viscous mass. The emulsion layer from the alkali washing was dissolved in a polar solvent, ethyl acetate, to isolate and remove any water that may have been present in the original emulsion layer. The remaining ethyl acetate solution was then combined with organic layer viscous mass, produced above, and the mixture concentrated by distillation to remove ethyl acetate and any remaining hexane. The concentrated mass was then subjected to high vacuum distillation and various fractions collected. Those fractions collected between oil bath temperatures of 190° C. and 270° C. and vapor temperature of from 140° C. to 180° C. were found to contain pure Bakuchiol with less than 0.05% by weight psoralene and isopsoralene. Those fractions collected between oil bath temperatures of 140° C. and 190° C. and vapor temperature of from 90° C. to 150° C. were subjected to column chromatographic purification to obtain pure Corylifolin with less than 0.1% psoralene. Purity was determined by HPLC analysis using a sample concentration of ≈0.5 mg/ml in acetonitrile, using a mobile phase composition of acetonitrile and water (70/30) with a flow rate of 1.0 ml/min., and a UV detector set at $\lambda_{max}$ 261 nm.

Example 1

Reduction of UV-Induced Erythema

Erythema, the most familiar manifestation of UV radiation exposure, occurs in a biphasic manner. UV-A mediates the early part of this reaction, known as immediate pigment darkening (IPD) and lasts for about half-hour. Delayed erythema, a function primarily of UV-B dosages, begins 2-8 hours after exposure and reaches a maximum in 24-36 hours, with erythema, pruritius, and pain in the sun-exposed areas.

Microscopically, changes are detectable as early as 30 minutes after UV radiation exposure. Epidermal changes include intracellular edema, vacuolization and swelling of melanocytes, and the development of characteristic sunburn cells. In the dermis, UV radiation initially leads to interstitial edema and endothelial cell swelling. Later, there is perivenular edema, degranulation, and toss of mast cells, a decrease in the number of Langerhans cells, neutrophil infiltration, and erythrocyte extravasation.

In order to evaluate the anti-erythematic properties of the sunscreen compositions of the present invention, a sample lotion, free of sunscreen actives, but containing the purified baktichiol, was applied to subjects who were then subjected to prolonged UV exposure. The sunscreen active was omitted so as expedite/exaggerate the manifestation of erythema that might otherwise be found with the sunscreen actives present. The lotion evaluated comprised the formulation set forth in Table 1.

The lotion was prepared by combining the Phase 1 ingredients, and then dispersing the Phase A-2 ingredient in the combined Phase A-1 composition while stirring and heating to a temperature of 75° C. Concurrently, the ingredients of Phase B were combined and heated to 75° C. Phase B was then added to Phase A with good mixing. Thereafter, the combined Phase A and B were homogenized at moderate speed, while adding Phases C and D. The complete mixture was allowed to cool to room temperature with constant propeller agitation until a homogeneous mixture was attained. The resultant mixture was found to have a pH of 6.20 and viscosity of 20,000 mPas (Brookfield RVT, Spindle C, 10 rpm) at 25° C.

TABLE 1

| Ingredient | Trade Name/Supplier | wt % |
|---|---|---|
| Phase A-1 | | |
| Water | Water(demineralized) | 78.70 |
| Disodium EDTA | Versene Na/Dow | 0.10 |
| Glycerine | Emery 916/Cognis | 3.00 |
| Phase A-2 | | |
| Xanthan Gum | Vanzan NF/Vanderbilt | 0.20 |
| Phase B | | |
| Caprylic/Capric Triglyceride | Myritol 318/Cognis | 6.00 |
| Squalane | Fitoderm/Centerchem | 1.00 |
| Cetyl Esters | Crodamol SS/Croda | 1.00 |
| Cetyl Alcohol | Crodacol C-70/Croda | 1.00 |
| Dimethicone | Dow Corning 200, 50 cst/Dow Corning | 2.00 |
| Glyceryl Stearate, PEG-100 Stearate | Arlacel 165/Uniquema | 3.50 |
| Bakuchiol | Sytenol ™ A/Sytheon | 1.00 |
| Phase C | | |
| Hydroxyethyl Acrylate/Sodium Acryloyldimethyl Taurate Copolymer & Squalane & Polysorbate 60 | Simulgel NS/Seppic | 1.50 |
| Phase D | | |
| phenoxyethanol, Methylparaben, propylparaben, Ethylparaben | Phenonip XB. Clariant | 1.00 |
| Total | | 100.00 |

In preparing for the erythema test, a 50 cm$^2$ test site on the backs of eleven human volunteers was subjected to seven UV exposures: the first lasting 25 seconds and each subsequent exposure lasting 25% longer than the previous, each exposure being made to a different portion of the test site, 16 to 24 hours later, the exposed areas of the human volunteers were evaluated using a chromameter to assess their MEDS (Minimal Erythematic Dose). Thereafter, the test lotion was applied at a rate of 2 mg/cm$^2$ twice a day for seven days to a test site measuring 4 cm×2.5 cm on the backs of each human volunteer. Following the completion of the application protocol, the test site and an untreated site of each volunteer were irradiated at 2× their MED. 16 to 24 hours following irradiation, the L and b parameters on both the treated and untreated sites were measured using a Chromameter. The changes in L values and ITA.degree (Individual Topology Angle—COLIPA SPF test method) were determined to assess erythema. ITA.degree. was calculated using the formula:

$$\text{ITA.degree.} = [\text{Arc Tangent}(L^* - 50)/b^*)]180/3.1416$$

wherein L*value—lightness and b*—color in blue-yellow axis. Table 2 presents the average L and ITA values of the treated and untreated skin for all human volunteers prior to irradiation or UV exposure ("Pre-Irr") and following irradiation or IJV exposure ("Post-Irr"). Table 2 also sets forth the delta or change in these values.

TABLE 2

|  | Pre-Irr | Post-Irr | Δ L, or ΔITA value |
| --- | --- | --- | --- |
| L-value (treated) | 65.69 | 66.25 | 0.56 |
| L-value (untreated) | 66.45 | 60.71 | −5.74 |
| ITA (treated) | 43.97 | 46.83 | −2.86 |
| ITA (untreated) | 46.05 | 36.76 | 9.29 |

As indicated by the results shown in Table 2, the degree of erythema as measured by a mechanical chromometer was markedly reduced in those areas that were treated with the bakuchiol containing lotion as compared to the untreated areas. To the naked eye, erythema in the treated areas was barely detectable though readily visible in the untreated areas. These results were surprising inasmuch as commercial grade Bakuchiol when used in skin treatments for, e.g., psoriasis, is shown to increase erythema.

Example 2

Collagenase Inhibitory Activity

In order to ascertain whether other benefits may be attained by the use of meroterpenes in sunscreen formulations, a study was conducted on the impact, if any, the presence of bakuchiol may have on collagenase: a collagenolytic enzyme responsible for much of the collagen damage associated with UV exposure and photoaging in general. Collagenase activity was measured with an Enzcheck kit from Molecular Probes (Carlsbad, Calif., USA) using quenched fluorescent gelatin and *Clostridium* collagenase IV, a generic metalloproteinase. Test material (aqueous solutions 1000 ug/ml, 100 ug/ml, 10 ug/ml and 1 ug/ml made from 10 mg/ml stock in DMSO) was incubated in the presence of collagenase substrate—quenched fluorescin-linked gelatin and in the presence of the proteolytic enzyme. Phenanthroline, a potent metalloprotease (MP) inhibitor was used as positive control at 100 ug/ml. The kinetics of the release of the digested, fluorescent gelatin were measured at excitation/emission wavelengths of 485/530 nm with Millipore Cytofluor 2350 microfluorometer. Collagenase inhibitory concentration 50% ($IC_{50}$ for the purified Bakuchiol was found to be ~0.1% (w/w).

These results indicate that the sunscreen formulations in accordance with the present invention would be expected to offer significant inhibition of collagenase as well as other damaging metalloproteiniase arising from UV exposure.

Example 3

Skin Sensitivity

Given the known sensitivity issues associated with commercial grade bakuchiol, evaluation of the skin sensitivity to the purified bakuchiol was also evaluated. Skin sensitivity was evaluated following the method cited in the reference *Appraisal of the Safety Chemicals in Food, Drugs and Cosmetics*, published by The Association of Food and Drug Officials of The United States. The method employs nine inductive patching and not the ten cited in the reference under occlusive patch conditions.

Samples were prepared for evaluation by diluting the purified Bakuchiol in corn oil to a 5% concentration, with dilutions freshly prepared on each application day. 0.2 ml or 0.2 g of the diluted test material was dispensed onto the occlusive, hypoallergenic patch and the treated patch applied directly to the skin of the infrascapular regions of the back, to the right or left of the midline of each subject: one hundred and eleven subjects were employed. After application of the patch, each subject was dismissed with instructions not to wet or expose the test area to direct sunlight. The patch was removed by the subject after 24 hours. This procedure was repeated every Monday, Wednesday and Friday for three consecutive weeks until a series of nine consecutive 24 hour exposures had been made. During the test period, the test area on the subjects' backs were observed for evidence of edema or erythema just before applications two through nine and the next test date following application nine. If evidence of a reaction was found, the area of edema and/or erythema was then measured and recorded: edema being estimated by an evaluation of the skin with respect to the contour of the unaffected normal skin. The subjects were then given a 10-14 day rest period after which a challenge or retest dose was applied once to a previously unexposed test site. The retest dose was equivalent to any one of the original nine exposures. Reactions were scored 24 and 48 hours after application. Based on the test results, the 5% dilution in corn oil of the purified bakuchiol was determined to be a NON-PRIMARY IRRITANT and a NON-PRIMARY SENSITIZER according to the reference.

Example 4

Purity and Coloration

Commercial acceptability of a sunscreen composition or a cosmetic composition is not based solely on its performance efficacy, but also on its appeal to the intended consumer and ease of use. One characteristic that affects it acceptability and ease of use is coloration. Other than those compositions which are intended to color one's skin, preference is to sunscreens that do not alter skin color and form a product that is aesthetically pleasing. Hence, most, if not all, sunscreen lotions and spays are either white or water clear. Even the long used zinc oxide products, which are famous for producing white noses, have been reformulated to provide a white cream which transforms to a clear film on application. Similarly, in cosmetics, the objective is to provide a natural skin appearance and while products are formulated for specific coloration, the addition of ingredients, especially darkly colored ingredients make formulations difficult or, simply cannot use such ingredients.

In this regard, two samples of bakuchiol were prepared or acquired to ascertain the effect of purity on color. In this study, a first sample, according to the preferred embodiment of the present teachings, was acquired from Sytheon Ltd. of Boonton, N.J. This product was found to have a purity of 95.5% (Bakuchiol A). A second sample, made in accordance with the teaching of Jia et. al. (US 2006/0251749), was found to have a purity of 82% w/w (Bakuchiol B). Both samples were found to be viscous liquids; however, Bakuchiol A was found to have a transparent, yellowish-tight amber color; whereas, Bakuchiol B had a dark blackish red color.

To assess the impact of this color on their utility, 0.5% w/w of each of Bakuchiol A and Bakuchiol B were added to separate samples of a typical serum formulation prepared by mixing together $C_{12-15}$ alkyl benzoate, cetearyl alcohol, glycerin, dimethicone, PPG 10 cetyl ether, arachidyl alcohol, methyl gluceth 20, behenyl alcohol, and $C_{13-14}$ isoparaffin. The formulation containing the Bakuchiol A was cream colored: a very common and amenable color for cosmetic compositions. On the other hand, the formulation containing Bakuchiol B was a darker brown color, almost that of chocolate ice-cream.

Example 5

Product Stability

In order to assess the impact of purity of the bakuchiol on the stability of a cosmetic composition, a further series of compositions were prepared as set forth in Table 3. Each of Bakuchiol A and Bakuchiol B were evaluated at three concentrations: 0.5, 1.0 and 2.0 weight percent. These formulations were prepared as follows: The components of each of Phase A and Phase B were separately combined and heated to 70-75° C. Phase A was added to Phase B while stirring. After mixing well, Phase A/B was homogenized allowing it to reach ~40° C. The Phase C components were then mixed with slight warming ~40° C. and, once combined, added to Phase A/B. Then the emulsion was cooled down to room temperature while stirring. Phase D was added while stirring until uniform, The pH of the two lotions was adjusted with triethanolamine to ~5.5 and the composition subsequently cooled down to room temperature while stirring.

Upon cooling, visible phase separation was noted within one week in the samples containing Bakuchiol B, especially those with the higher concentration. In contrast, there was no indication of any precipitation/phase separation in the case of any of the formulations made with Bakuchiot A, even after standing at room temperature for over three months. Additionally, there was a distinct color change in those formulations made with Bakuchiol B, which tended to turn very dark, especially at the higher concentrations; whereas, those formulations made with the Bakuchiol A showed little if any color change over the test period, even at the higher concentrations.

These results indicate the storage stability and suitability from a commercial standpoint of the high purity bakuchiol, i.e., greater than 90% w/w, even as compared to bakuchiol have even a modest drop in purity, down to 82% w/w. For the purpose of this application and the appended claims, the term "storage stable" or "storage stability" refers to a lack of precipitation, phase separation and/or color change in the claimed compositions as compared to a similar composition but with a less pure, e.g., 82% w/w, meroterpene.

Example 6

Sunscreen Formulations 6A-6J

The following tables set forth various formulations and embodiments of sunscreens according to the present invention. Following each table is a brief description of the process by which each formulation is made.

TABLE 3

| Ingredient | Trade Name/Supplier | Bakuchiol A | Bakuchiol B |
|---|---|---|---|
| Phase A | | | |
| Glyceryl stearate and PEG-100 | Arlacel 165/Uniqema | 1.5 | 1.5 |
| Arachidyl alcohol, Behenyl alcohol, Arachidyl glucoside | Montanov 202/Seppic | 4.00 | 4.00 |
| Dimethyl isosorbide | Arlasolve DMI/Uniqema | 3.00 | 3.00 |
| Isohexadecane | Permethyl 101A/Presperse | 8.00 | 8.00 |
| Dimethicone | Dow Corning 200, 100 cst/Dow Corning | 2.00 | 2.00 |
| Bakuchiol | | 0.50/1.00/2.00 | 0.5/1.00/2.00 |
| Phase B | | | |
| Water | | QS to 100 | QS 100 |
| Propylene Glycol | Propylene glycol/Lyondell | 2.00 | 2.00 |
| Pentylene Glycol | Hydrolite-5/Symrise | 3.00 | 3.00 |
| Xanthan Gum | Vanzan NF/Vanderbilt | 0.25 | 0.25 |
| Phase C | | | |
| Cyclomethicone | Dow Corning 344/Dow Corning | 4.00 | 4.00 |
| Hydroxyethylacrylate (and) sodium acryloyldimethyl taurate copolymer | Sepinove EMT 10/Seppic | 1.00 | 1.00 |
| Phenoxyethanol, Methylparaben, Propylparaben, Ethylparaben | Phenonip XB. Clariant | 1.00 | 1.00 |
| Phase D | | | |
| Pentylene glycol | Hydrolite-5/Symrise | 3.00 | 3.00 |
| Dimethyl isosorbide | Arlasolve DMI/Uniqema | 3.00 | 3.00 |
| Salicylic acid | | 2.00 | 2.00 |
| Total | | 100.00 | 100.00 |

| Formulation 6A: Sunscreen Lotion | | |
| --- | --- | --- |
| INCI Name | Trade Name/Supplier | % W/W |
| Phase A | | |
| Water (demineralized) | | 57.25 |
| Disodium EDTA | | 0.10 |
| Propylene Glycol | | 2.00 |
| Sorbitol | Sorbo (70% soln.)/Uniqema | 2.00 |
| Sodium Lauryl Sulfate | Stepanol ME-Dry/Stepan | 0.15 |
| Phase B | | |
| Glyceryl Stearate | Tegin M/Goldschmidt | 5.00 |
| Stearic acid | Emersol 132/Cognis | 1.00 |
| *Persea Gratissima* (Avocado) oil Unsaponifiables | Crodarom Avocadin/Croda | 15.00 |
| Avobenzone (sunscreen) | Eusolex 9020/EMD | 2.00 |
| Diethylhexyl syringylidene malonate (photostabilizer) | Oxynex ST/EMD | 2.00 |
| Homosalate (sunscreen) | Eusolex HMS/EMD | 10.00 |
| Beeswax | White Bleached NF Beeswax Prills/Ross | 1.50 |
| Bakuchiol | Present Invention | 1.00 |
| Phase C | | |
| Triethanolamine | TEA 99%/Union Carbide | qs |
| Phase D | | |
| Propylene glycol, DMDM Hydantoin, Methylparaben | Paragon/McIntyre | 1.00 |
| Total | | 100.00 |

Formulation 6A is prepared by separately combining the ingredients of Phases A and B and heating each mixture to 70-75° C. Thereafter, Phases A and B are combined while stirring. The pH is adjusted to 5.0-6.0 by the addition of Phase C to the mixture of Phases A and B. Subsequently, Phase D is added with mixing until a uniform, substantially homogenous mixture is attained.

| Formulation 6B - Daily Sunscreen Lotion | | |
| --- | --- | --- |
| INCI Name | Trade Name/Supplier | % W/W |
| Phase A-1 | | |
| Water (demineralized) | | 48.18 |
| Disodium EDTA | | 0.05 |
| Propylene Glycol | | 5.00 |
| Niacinamide | | 2.00 |
| Phase A-2 | | |
| Xantham Gum | Vanzan NF/Vanderbilt | 0.25 |
| Magnesium aluminum stearate | Veegum Ultra granules/Vanderbilt | 0.40 |
| Phase B | | |
| Cetearyl alcohol and cetearyl glucoside | Montanov 68/Seppic | 7.00 |
| Apricot Kernel oil | Lipovol P/Lipo | 5.00 |
| Octyl stearate | Cetiol 868/Cognis | 3.00 |
| Dimethicone | Dow Corning 200 fluid 10 cst/Dow Corning | 6.00 |
| Octinoxate (sunscreen) | Eusolex 2292/EMD | 7.5 |
| Homosalate (sunscreen) | Eusolex HMS/EMD | 12.5 |
| *Psoralea corylifolia* purified plant extract containing 65% Bakuchiol | Present Invention | 2.00 |
| Phase C | | |
| Triethanolamine | TEA 99% Union Carbide | 0.12 |
| Phase D | | |
| Phenoxyethanol, Isopropylparaben, Isobutylparaben, butylparaben | Liquapar PE/Sutton | 1.00 |
| Total | | 100.00 |

Formulation 6B is prepared by separately combining the constituents of each of Phases A-1 and A-2. Thereafter, Phase A-2 is dispersed in Phase A-1 and heated to 70-75° C. The mixture of Phase B is then heated to 70-75° C. and added to the Phase A-1/A-2 dispersion with constant stirring. The mixture is homogenized until it cools to 60° C. Thereafter the pH is adjusted to 4.0-5.0 using Phase C. Thereafter, Phase D is added to the mixture and the mixture continually mixed until uniform, substantially homogeneous lotion is achieved.

| Formulation 6C: Skin Rejuvenating Sunscreen Lotion | | |
| --- | --- | --- |
| INCI Name | Trade Name/Supplier | % W/W |
| Phase A-1 | | |
| Water (demineralized) | | 43.65 |
| Disodium EDTA | | 0.05 |
| Propylene Glycol | | 5.00 |
| Phase A-2 | | |
| Xanthan Gum | Vanzan NF/Vanderbilt | 0.20 |
| Phase B | | |
| PEG-6 stearate, ceteth-20, glyceryl strearate, steareth-20, stearic acid | Tefose 2561/Gattefosse | 10.00 |
| Stearic Acid | Emersol 132/Cognis | 1.00 |
| Hydrogenated castor oil | Cutina HR/Cognis | 1.00 |
| Octyldodecyl myristate | M.O.D./Gattefosse | 8.00 |
| Dimethicone | Dow Corning 200, 50 cst/Dow Corning | 4.00 |
| Phenyltrimethicone | Dow Corning 556 Wax/Dow Corning | 2.00 |
| Avobenzone (sunscreen) | Eusolex 9020 | 3.00 |
| Octocrylene (sunscreen) | Eusoloex OCR | 7.00 |
| Homosalate (sunscreen) | Eusolex HMS | 10.00 |
| Phase C | | |
| Sweet Almond oil | Cropure Almond/Croda | 3.00 |
| Bakuchiol | Present Invention | 1.00 |
| Phase D | | |
| Triethanolamine | TEA 99%/Union Carbide | 0.10 |
| Phase E | | |
| Phenoxyethanol, Isopropylparaben, Isobutylparaben, butylparaben | Liquapar PE/Sutton | 1.00 |
| Total | | 100.00 |

Formulation 6C is made by dispersing Phase A-2 in the pre-mixed Phase A-1 and heating to 70-75° C. Concurrently, the ingredients of Phase B are combined and heated to 70-75° C. and then that mixture added to the Phase A-1/A-2 mixture while stirring. The combined mix is homogenized until the mixture cools to 60° C. Phase C is then added at 40° C. The pH is then adjusted to 5.0-6.0 with phase D. Thereafter, Phase E is added and mixed until a uniform, substantially homogeneous mixture is attained.

| Formulation 6D: Broad-Spectrum Sunscreen | | |
|---|---|---|
| INCI Name | Trade Name | % W/W |
| Phase A | | |
| Avobenzone (sunscreen) | Eusolex 9020 | 1.00 |
| Glyceryl Stearate, Cetareth-15 | Tego Care 215, Pellets | 3.00 |
| Decyl Oleate | Cetiol V | 5.00 |
| Isopropyl Palmitate | — | 5.00 |
| Dimethicone | Mirasil DM 350 | 0.50 |
| Stearyl Alcohol | Lanette 18 | 2.00 |
| Carbomer | Carbopol ETD 2050 | 0.10 |
| Phase B | | |
| Glycerin (about 87%) | Glycerol | 3.00 |
| Ectoin | RonaCare Ectoin | 0.50 |
| Preservative | | 1.00 |
| Water, Ethyhexyl methoxycinnamate (sunscreen), Silica, PVP, Chlorphenesin, BHT | Eusolex UV-Pearls OMC | 15.00 |
| Water | Water, deminaralized | q.s |
| Phase C | | |
| Corylifolin | Present Invention | 0.50 |
| Phase D | | |
| Sodium hydroxide | Sodium hydroxide, 10% solution | 0.45 |
| Phase E | | |
| Perfume | Fragrance "Delicat" | 0.20 |
| Total | | 100.00 |

The ingredients of Phase A and Phase B are separately combined and each mixture heated to 80° C. Phases A and B are then combined with constant stirring. The combined mix is homogenized until the mixture cools to 60° C. Phase C is then added at 40° C. The pH is then adjusted to 5.0-6.0 with phase D. Thereafter, Phase E is added and mixed until a uniform. Substantially homogeneous mixture is attained.

| Formulation 6E: Sunburn Responsive and Skin Rejuvenating Sunscreen | | |
|---|---|---|
| INCI Name | Trade Name/Supplier | % w/w |
| Phase A-1 | | |
| Water (demineralized) | | 42.20 |
| Disodium EDTA | | 0.05 |
| Propylene Glycol | | 5.00 |
| Phase A-2 | | |
| Xantham Gum | Vanzan NF/Vanderbilt | 0.20 |
| Phase B | | |
| PEG-6 stearate, ceteth-20, glyceryl stearate, steareth-20, stearic acid | Tefose 2561/Gattefosse | 10.00 |
| Stearic Acid | Emersol 132/Cognis | 1.00 |
| Hydrogenated castor oil | Cutina HR/Cognis | 1.00 |
| Octyldodecyl myristate | M.O.D./Gattefosse | 8.00 |
| Dimethicone | Dow Corning 200, 50 cst/Dow Corning | 4.00 |
| Phenyltrimethicone | Dow Corning 556 Wax/Dow Corning | 2.00 |
| Avobenzone (sunscreen) | Eusolex 9020/EMD | 1.00 |
| Octocrylene (sunscreen) | Eusolex OCR/EMD | 2.00 |
| Homsalate (sunscreen) | Eusolex HMS/EMD | 10.00 |
| Phase C | | |
| Sweet Almond oil | Cropure Almond/Croda | 3.00 |
| Bisabolol | Bisabolol/Rona | 1.00 |
| Corylifolin | Present invention | 2.00 |
| Phase D | | |
| Phyllanthus emblica fruit extract | Emblica/EMD | 0.50 |
| Water (dimineralized) | | 5.00 |
| Phase E | | |
| Aminomethyl propanol | | 0.05 |
| Phase F | | |
| Phenoxyethanol, Isopropylparaben, Isobutylparaben, Butylparaben | Liquapar PE/Sutton | 1.00 |
| Total | | 100.00 |

Formulation 6E is made by separately combining the components of Phase A-1 and Phase A-2. Phase A-2 is then dispersed in Phase A-1 and heated to 70-75° C. Concurrently, the ingredients of Phase B are combined and heated to 70-75° C. and then that mixture added to the Phase A-1/A-2 dispersion while stirring. The combined mix is homogenized until the mixture cools to 60° C. Phase C is then added at 30° C. with constant stirring using a propeller mixer. The pH is then adjusted to 5.0-6.0 with phase D. Thereafter, Phases E and F are sequentially added and mixed under dark conditions until a uniform mixture is attained.

| Formulation 6F: Anhydrous Oil-Free Sunscreen Gel | | |
|---|---|---|
| INCI Name | Trade Name/Supplier | % W/W |
| Phase A | | |
| Ozokerite | White Ozokerite SP-1020/Strahl & Pitsch | 3.00 |
| Cyclomethicone | Dow Corning 345 Fluid/Dow Corning | 20.00 |
| Cyclomethicone (and) Polysilicone-11 | Gransil GCM/Grant Industries | 52.50 |
| Octinoxate (sunscreen) | Eusolex 2292/EMD | 7.50 |
| Homsalate (sunscreen) | Eusolex HMS/EMD | 5.00 |
| Phase B | | |
| Bismuth Oxychloride | Biron ® LF-2000/Rona | 2.00 |
| Phase C | | |
| Cyclomethicone | Dow Corning 345 Fluid/Dow Corning | 3.60 |
| Cyclomethicone (and) Dimethicone Crosspolymer | Dow Corning 9040 Silicone Elastomer Blend/Dow Corning | 5.40 |
| Bakuchiol | Present Invention | 1.00 |
| Total | | 100.00 |

Formulation 6F is prepared by blending the Phase A ingredients while heating to 70-75° C. and mixing until clear and uniform mixture is obtained. Phase B is then dispersed in the Phase A mixture with mixing. The Phase C ingredients are separately blended until the mixture is smooth and substantially free of lumps. The Phase A/B mixture is then cooled to 50-60° C. and Phase C added with mixing until a substantially uniform mixture is obtained.

| Formulation 6G: Self-Tanning Sunscreen Spray Lotion | | |
| --- | --- | --- |
| INCI Name | Trade Name/Supplier | % w/w |
| Phase A | | |
| Glyceryl Stearate, Ceteareth-20, Cetearyl Alcohol, Ceteareth-12, Cetyl Palmitate | Emulgade SE/Henkel | 4.50 |
| Ceteareth-20 | Eumulgin B2/Henkel | 1.00 |
| Dicapryl Ether | Cetiol OE/Henkel | 5.00 |
| Coco Caprylate/Caprate | Cetiol LC/Henkel | 5.00 |
| Octinoxate (sunscreen) | Eusolex 2292/EMD | 7.00 |
| Octisalate (sunscreen) | Eusolex OS/EMD | 5.00 |
| Oxybenzone (sunscreen) | Eusolex 4360/EMD | 2.00 |
| Phase B | | |
| Demineralized water | | 39.45 |
| Disodium EDTA | | 0.05 |
| Phase C | | |
| 3-Hydroxy Bakuchiol | Present invention | 1.50 |
| Phase D | | |
| Demineralized water | | 20.00 |
| Propylene glycol | | 2.50 |
| Dihydroxyacetone | Dihydroxyacetone/EMD | 6.00 |
| Propylene Glycol (and) DMDM Hydantoin (and) Methylparaben | Paragon/McIntyre | 1.00 |
| Total | | 100.00 |

Formulation 6G is prepared by combining the Phase A ingredients while stirring and heating to 80-85° C. Phase B is heated to 80-85° C. and slowly Phase A is added to Phase B while stirring with a propeller mixer. Homogenize the Phase A/B mixture and allow the mixture to cool to around 40° C. Phase C is then added and mixed well. Separately, the ingredients of Phase D are combined at room temperature by stirring. Once the Phase A/B/C mixture is cooled to 30° C., Phase D is then added with mixing. If necessary, the pH may be adjusted to 3.5-4.0 using citric acid. The mixture should have a viscosity <100 cps as measured by a Brookfield RV#1, 50 rpm @ 23° C.

| Formulation 6H: Sunscreen Cream | | |
| --- | --- | --- |
| INCI name | Trade Name/Supplier | % w/w |
| Phase A | | |
| Titanium Dioxide (sunscreen), Alumina, Simethicone | Eusolex ® T-2000/Rona | 10.00 |
| Polyglyceryl-2 Dipolyhydroxystearate | Dehymuls PGPH/Cognis | 4.00 |
| Polyglyceryl-3 Diisostearate | Lamaform TGI FL/Cognis | 2.00 |
| Beeswax | Beeswax White SP 422/Strahl & Pitsch | 3.00 |
| Isostearic Acid | Emersol 871/Cognis | 1.00 |
| Zinc Stearate | Unichem ZS/Universal Preser-A- Chem | 1.00 |
| Dicaprylyl Carbonate | Cetiol CC/Cognis | 11.00 |
| Tocopherol (antioxidant) | Vitamin E/Hoffmann- La Roche | 2.00 |
| 3-Hydroxy Bakuchiol | Present Invention | 5.00 |
| Propylparaben | Nipasol M/Clariant | 0.05 |
| Phase B | | |
| Water (demineralized) | | 44.30 |
| Magnesium Sulfate | Magnesium Sulfate Heptahydrate/Rona | 1.00 |
| Methylparaben | Nipagin M/Clariant | 0.15 |
| Glycerin | Emery 916/Cognis | 5.00 |
| Phase C | | |
| Bisabolol | RonaCare ® Bisabolol/Rona | 0.50 |
| Total | | 100.00 |

Formulation 6H is prepared by separately combining the ingredients of Phase A and Phase B and heating each mixture to 80° C. Phase B is then added slowly to phase A while stirring. The mixture is homogenized at 65-55° C. and then cooled while stirring. Once the temperature reaches 40° C., Phase C is added and the mixture mixed until uniform.

| Formulation 6I: Broad Spectrum Sunscreen Lotion | | |
| --- | --- | --- |
| INCI name | Trade Name/Supplier | % w/w |
| Phase A-1 | | |
| Deionized water | | 64.95 |
| Disodium EDTA | | 0.10 |
| Propylene Glycol | | 3.00 |
| Glycerin | | 2.00 |
| Phase A-2 | | |
| Acrylates/C10-30 Alkyl Acrylate Copolymer | Carbopol EDT 2020/Goodrich | 0.15 |
| Xanthan Gum | Vanzan NF/Vanderbilt | 0.15 |
| Phase B | | |
| Cetyl alcohol, glyceryl stearate, PEG-75, ceteth-20 and steareth-20 | Emolium Delta/Gattefosse | 4.00 |
| Bakuchiol | Present invention | 1.00 |
| Dimethicone | DC200 fluid, 100 cst/Dow | 0.50 |
| C30-38 Olefin/Isopropyl Maleate/ MA Copolymer | Performa V1608/New Phase Technologies | 1.00 |
| C12-15 Alkyl benzoate | Finsolv TN/Finetex | 10.00 |
| Avobenozne (sunscreen) | Eusolex 9020/RONA | 2.00 |
| Diethylhexyl syringylidene malonate (photostabilizer) | Oxynex ST/RONA | 2.00 |
| Homosalate (sunscreen) | Eusolex HMS/RONA | 8.00 |
| Phase C | | |
| Triethanolamine (99%) | TEA 99%/Union Carbide | 0.15 |
| Phase D | | |
| Phenoxyethanol (and) Isopropylparaben (and) Isobutylparaben (and) Butylparaben | Liquapar PE/ISP | 1.00 |
| Total | | 100.00 |

Formulation 6I is prepared by separately combining the ingredients of Phase A-1 Phase A-2. Phase A-2 is then dispersed in the Phase A-1 mixture with agitation and heated to 75° C. Separately, the Phase B ingredients are combined and heated to 75° C. The Phase B mixture is then added to the Phase A-1/A-2 dispersion with continuous stirring. The mixture is homogenized for 10 min and cooled to 45° C. Phases C and D are then sequentially added and mixed until uniform.

| Formulation 6J: Self-Tanning Sunscreen Lotion | | |
|---|---|---|
| INCI Name | Trade Name/Supplier | % w/w |
| Phase A | | |
| Deionized Water | | 39.15 |
| Xanthan Gum | Keltrol/Kelco | 0.75 |
| Propylene Glycol | Propylene Glycol | 5.00 |
| Methylparaben | | 0.20 |
| Propylparaben | | 0.10 |
| Phase B | | |
| Steareth-10 | Brij 76/ICI | 0.70 |
| Glyceryl Stearate (and) PEG-100 Stearate | Arlacel 165/ICI | 1.20 |
| PEG-40 Stearate | Myrj 52-S/ICI | 0.40 |
| Cetearyl Alcohol (and) Ceteareth-20 | Cosmowax J/Croda | 1.00 |
| Cetearyl Alcohol | | 1.50 |
| Cyclomethicone | Dow Corning 344 Fluid/Dow Corning | 5.00 |
| Dimethicone | Dow Corning 200 Fluid 100 cst/Dow Corning | 0.50 |
| Octyldodecyl Neopentanoate | Elefac I-205/Bernel | 16.50 |
| Avebenzone (sunscreen) | Eusolex 9020/EMD | 1.00 |
| Diethylhexylsyringylidene malonate (photostabilizer) | Oxynex ST/EMD | 1.00 |
| Homosalate (sunscreen) | Eusolex HMS/EMD | 5.00 |
| Octisalate (sunscreen) | Eusolex OS/EMD | 5.00 |
| Phase C | | |
| Bakuchiol | Present invention | 2.00 |
| Phase D | | |
| Deionized Water | | 10.00 |
| Dihydroxyacetone | Dihydroxyacetone/Rona | 5.00 |
| Total | | 100.00 |

Formulation 6J is prepared by charging the Phase A water component to a mixing vessel. Under low homogenization, the Phase A xanthan gum is sprinkled in and mixed to uniformity. The remaining Phase A ingredients are then added while maintaining homogenization and the mixture heated 75-80° C. The Phase B ingredients are mixed in a separate vessel and heated to 85° C. An emulsion is prepared by adding Phase B to Phase A and adjusting the homogenizer speed as necessary to ensure adequate batch turnover. The homogenized mixture is then held at 85° C. for 10 minutes after which mixing is then switched from homogenization to impeller mixing at 60° C. The mixture is allowed to cool and Phase C is added at around 40° C. and mixed welt. The Phase D ingredients are separately mixed at room temperature with constant mixing to ensure uniformity. The Phase D mixture is then added to Phase A/B/C mixture at 40° C. and continually mixed until the mixture reaches room temperature.

In any of the formulations set forth above, the meroterpene identified could just as readily be substituted with another meroterpene such as bakuchiol, corylifolin, hydroxy-bakuchiol, etc. Additionally, these formulations are preferably stored and packaged in tinted vessels/containers so as to prevent their exposure to light, especially UV light, until use. This is especially important for those formulations employing organic UV absorbers that are chemically altered and/or rendered inactive once a given amount of UV light is absorbed.

Similarly, while the foregoing formulations contain many ingredients other than the critical ingredients including surfactants, stabilizers, self-tanning agents, antioxidants and the like, these additional ingredients could just as easily have been omitted without compromising the sunscreen and anti-erythema properties thereof.

Without further elaboration, it is believed that one skilled in the art can, using the preceding description, can utilize the present invention to its fullest extent. Furthermore, while the present invention has been described with respect to aforementioned specific embodiments and examples, it should be appreciated that other embodiments utilizing the concept of the present invention are possible, and within the skill of one in the art, without departing from the scope of the invention. The preceding preferred specific embodiments are, therefore, to be construed as merely illustrative, and not limitative of the remainder of the disclosure in any way whatsoever.

What is claimed is:

1. A sunscreen composition for preventing or lessening sun-induced damage to human skin comprising a storage stable emulsion of (i) at least one UV-B or UV-A/UV-B sunblock active, or a combination thereof, in a conventional amount, (ii) from about 0.1 to about 10 weight percent of at least one meroterpene and (iii) dermatological acceptable carrier, wherein said meroterpene (a) is a compound having the structure:

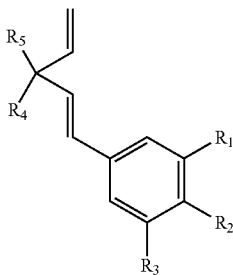

wherein $R_1$, $R_2$, and $R_3$ are each independently selected from the group consisting of H, OH, $OR_6$ or $CH_2R_6$ where $R_6$ is linear or branched $C_1$ to $C_8$ alkyl; $R_4$ and $R_5$ are each independently a linear or branched, $C_1$ to $C_{20}$ alkyl or alkenyl group, (b) is free or substantially free of psoralens, and (c) has a purity of at least 90% w/w.

2. The sunscreen composition of claim 1 wherein the meroterpene has a purity of at least 95% w/w.

3. The sunscreen composition of claim 1 wherein the meroterpene is present in an amount of from about 0.5 to 5 percent by weight.

4. The sunscreen composition of claim 1 wherein the meroterpene is free or substantially free of furanocoumarins.

5. The sunscreen of claim 1 wherein the meroterpene is selected from the group consisting of bakuchiol, hydroxy-bakuchiol, corylifolin, or a combination or any two or more thereof.

6. The sunscreen composition of claim 1 wherein the meroterpene is bakuchiol.

7. The sunscreen composition of claim 1 further comprising one or more skin protective and/or treatment ingredients selected from the group consisting of antioxidants, vitamins, anti-inflammatory agents, self-tanning agents, moisturizers, emollients, humectants, and mixtures thereof.

8. An improved storage stable emulsive sunscreen composition wherein the improvement, comprises the presence of from about 0.1 to about 10 weight percent of at least one meroterpene (a) having the structure:

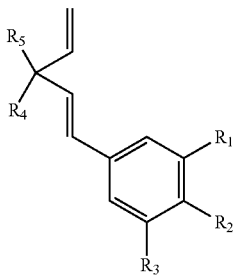

wherein $R_1$, $R_2$, and $R_3$ are each independently selected from the group consisting of H, OH, $OR_6$ or $CH_2R_6$ where $R_6$ is linear or branched $C_1$ to $C_8$ alkyl; $R_4$ and $R_5$ are each independently a linear or branched, $C_1$ to $C_{20}$ alkyl or alkenyl group, (b) that is free or substantially free of psoralens, and (c) has a purity of at least 90% w/w.

9. The sunscreen composition of claim 8 wherein the meroterpene has a purity of at least 95% w/w.

10. The sunscreen composition of claim 8 wherein the meroterpene is present in an amount of from about 0.5 to 5 percent by weight.

11. The sunscreen composition of claim 8 wherein the meroterpene is a free or substantially free of furanocoumarins.

12. The sunscreen composition of claim 8 wherein the meroterpene is bakuchiol.

13. The sunscreen composition of claim 8 further comprising one or more skin protective and/or treatment ingredients selected from the group consisting of antioxidants, vitamins, anti-inflammatory agents, self-tanning agents, moisturizers, emollients, humectants, and mixtures thereof.

14. A method of preparing a storage stable emulsive sunscreen composition, said method comprising emulsifying (i) at least one UV-B or UV-A/UV-B sunblock active, or a combination thereof, in a conventional amount, (ii) from about 0.1 to about 10 weight percent of at least one meroterpene and (iii) a dermatological acceptable carrier, wherein said meroterpene (a) is a compound having the structure:

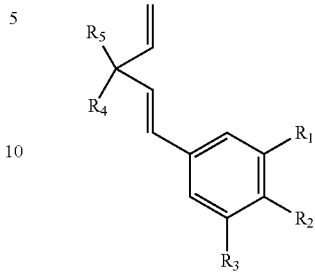

wherein $R_1$, $R_2$, and $R_3$ are each independently selected from the group consisting of H, OH, $OR_6$ or $CH_2R_6$ where $R_6$ is linear or branched $C_1$ to $C_8$ alkyl; $R_4$ and $R_5$ are each independently a linear or branched, $C_1$ to $C_{20}$ alkyl or alkenyl group, (b) is free or substantially free of psoralens, and (c) has a purity of at least 90% w/w.

15. The method of claim 14 wherein the meroterpene has a purity of at least 95% w/w.

16. The method of claim 14 wherein the sunscreen composition further comprises at least one UV-A sunblock active.

17. The method of claim 14 wherein the meroterpene is present in an amount of from about 0.5 to 5 percent by weight.

18. The method of claim 14 wherein the meroterpene is selected from the group consisting of bakuchiol, hydroxybakuchiol, corylifolin, or a combination or any two or more thereof.

19. The method of claim 14 wherein the meroterpene is bakuchiol.

20. The sunscreen composition of claim 14 further comprising one or more skin protective and/or treatment ingredients selected from the group consisting of antioxidants, vitamins, anti-inflammatory agents, self-tanning agents, moisturizers, emollients, humectants, and mixtures thereof.

* * * * *